(12) United States Patent
Yan et al.

(10) Patent No.: US 12,130,272 B1
(45) Date of Patent: Oct. 29, 2024

(54) DEVICE AND METHOD FOR FIELD IN-SITU MULTI-PLOT SYNCHRONOUS MONITORING OF GREENHOUSE GAS FLUXES

(71) Applicant: Institute of Soil Science, Chinese Academy of Sciences, Nanjing (CN)

(72) Inventors: Xiaoyuan Yan, Nanjing (CN); Wei Zhou, Nanjing (CN)

(73) Assignee: Institute of Soil Science, Chinese Academy of Sciences, Nanjing (CN)

( * ) Notice: Subject to any disclaimer, the term of this patent is extended or adjusted under 35 U.S.C. 154(b) by 0 days.

(21) Appl. No.: 18/741,455

(22) Filed: Jun. 12, 2024

(30) Foreign Application Priority Data

Jan. 25, 2024 (CN) .......................... 202410103393.2

(51) Int. Cl.
*G01N 33/00* (2006.01)
*G01N 33/24* (2006.01)

(52) U.S. Cl.
CPC ..... *G01N 33/0075* (2013.01); *G01N 33/0022* (2013.01); *G01N 33/0068* (2024.05); *G01N 33/245* (2024.05)

(58) Field of Classification Search
CPC ........... G01N 33/0075; G01N 33/0022; G01N 33/0068; G01N 33/245
See application file for complete search history.

(56) References Cited

U.S. PATENT DOCUMENTS 8,712,692 B2 * 4/2014 Risk .................... G01N 1/2294
73/23.32

FOREIGN PATENT DOCUMENTS

| CN | 201078754 Y | 6/2008 | | |
|----|----|----|----|----|
| CN | 203572823 U | 4/2014 | | |
| CN | 104316645 A | 1/2015 | | |
| CN | 106525135 A | 3/2017 | | |
| CN | 106885875 A | * | 6/2017 | |
| CN | 108318607 A | * | 7/2018 | ............... G01N 1/22 |
| CN | 212083224 U | 12/2020 | | |
| CN | 113358426 A | 9/2021 | | |
| KR | 10-0992876 B1 | 11/2010 | | |
| KR | 10-2012-0063015 A | 6/2012 | | |
| KR | 10-2013-0050035 A | 5/2013 | | |
| KR | 20150114672 A | * | 10/2015 | |
| KR | 10-2016-0075394 A | 6/2016 | | |

* cited by examiner

*Primary Examiner* — Kristina M Deherrera
*Assistant Examiner* — Fatemeh Esfandiari Nia
(74) *Attorney, Agent, or Firm* — MUNCY, GEISSLER, OLDS & LOWE, P.C.

(57) ABSTRACT

A device and method for field in-situ multi-plot synchronous monitoring of greenhouse gas fluxes, wherein a transparent plexiglass chamber is fixed to a stainless steel base, and the plexiglass chamber is provided with two movable square plexiglass plates; the square plexiglass plates are connected to the plexiglass chamber through push rods, and the push rods are configured to close or open the square plexiglass plates, so to seal or communicate the plexiglass chamber; sampling tubes are arranged on side walls of the plexiglass chamber; one ends of sampling pumps are connected to the sampling tubes; one end of each sucking pump is connected to each sampling tube through a solenoid valve, and the other end of each sucking pump is connected to a gas analyzer through a switch; and the gas analyzer is connected to a computer host, configured to measure concentration data of gas in the sampling tubes.

4 Claims, 5 Drawing Sheets

DEVICE AND METHOD FOR FIELD IN-SITU MULTI-PLOT SYNCHRONOUS MONITORING OF GREENHOUSE GAS FLUXES

TECHNICAL FIELD

The present invention relates to the technical field of environmental monitoring, and in particular, to a device and method for field in-situ multi-plot synchronous monitoring of greenhouse gas fluxes.

BACKGROUND

Trace gases such as $CO_2$, $CH_4$, and $N_2O$ will inevitably be emitted to the atmosphere during agricultural production due to the action of soil microorganisms. It is estimated that 8% of global anthropogenic $CH_4$ emissions and 50% of anthropogenic $N_2O$ emissions come from farmland. Finding a scientific and reasonable planting mode that reduces greenhouse gas emissions while ensuring stable crop yields is a must way for sustainable agricultural development. To this end, a large number of field experiments need to be carried out to monitor farmland greenhouse gas emissions at a high frequency, so as to provide a scientific basis for the development of reliable farmland carbon sequestration and emission reduction technologies.

At present, eddy correlation and static chamber methods are commonly used to observe gas fluxes. The eddy correlation method requires a large area (more than 1 hectare) of uniform farmland with no other emission sources in the vicinity, and also requires high-precision precise instruments. Since the requirements for experimental fields are relatively high, and the instruments and equipment that need to be purchased are expensive, the eddy correlation method is mostly used for long-term single-point observation research in large zones. The chamber method mostly uses plastic materials to form a relatively closed space in the field, and measures the change in gas concentration per unit time to calculate a flux. This method has the advantages of small occupied area and simple structure, is especially suitable for comparative studies on field plots, and is a commonly used observation method for greenhouse gas fluxes in farmland. The chamber method requires manual sampling, and bringing the collected samples back indoors for measurement is time-consuming and labor-intensive and is prone to human error. In addition, there is an obvious day-night difference in soil greenhouse gas emission, which is mainly affected by environmental conditions such as soil temperature, moisture, nutrients, light, etc. Therefore, it is usually necessary to monitor diurnal flux changes before sampling to determine the appropriate sampling time to represents the average of a daily flux. This is very difficult for manual sampling. The automatic observation method developed later, which uses an automatic open top chamber and a gas analyzer jointly, realizes automatic observation, but cannot monitor several experimental plots simultaneously, which will bring great errors to experimental results. Flux monitoring requires continuous monitoring of changes in greenhouse gas concentration in sampling chambers within a certain period of time (usually 30 minutes). The traditional continuous observation method generally involves a single sequential measurement. For example, when 6 experimental plots need to be monitored, it should sequentially rather than synchronous monitor the plots, the time interval between the first sampling and the last sampling will be more than 3 hours. This will bring great difference to monitoring data due to diurnal variations of flux, which will cover the differences caused by experimental processing, thus affecting the accuracy of experimental results. When conducting research on farmland carbon sequestration and emission reduction technologies, it is often necessary to conduct field verification experiments involving a plurality of measures. Each measure requires at least three repetitions, resulting in a large number of plots. Taking 48 plots as an example, if the traditional continuous observation method is used, the time interval between the first experimental plot and the last experimental plot will be as much as 24 hours. Such a long interval may affect the comparability of data, making it impossible to accurately evaluate the emission reduction effects between different measures, thus affecting the formulation of relevant technical standards and management policies.

Therefore, it is necessary to establish a technology that can realize field in-situ multi-plot synchronous monitoring of greenhouse gas fluxes, so as to avoid the errors caused by asynchronous sampling time of the traditional method.

SUMMARY

In order to overcome the defects of the prior art, an object of the present invention is to provide a device and method for field in-situ multi-plot synchronous monitoring of greenhouse gas fluxes.

To achieve the above object, the present invention provides the following schemes:

A device for field in-situ multi-plot synchronous monitoring of greenhouse gas fluxes, including at least one independent monitoring channel and a gas measurement and data processing system connected to the independent monitoring channel, the monitoring channel including:

an automatic open top chamber system, including a stainless steel base, a plexiglass chamber, push rods, fans, sampling tubes and a temperature and humidity sensor, where the stainless steel base is arranged in target soil, the bottom of the plexiglass chamber is fixed to the stainless steel base and is transparent, the top of the plexiglass chamber is provided with two movable square plexiglass plates, the square plexiglass plates are connected to the plexiglass chamber through the push rods, and the push rods are configured to close the square plexiglass plates to seal the plexiglass chamber or to open the square plexiglass plates to communicate the plexiglass chamber with the outside world; the fans are arranged on an upper side wall of the plexiglass chamber and at the same position opposite the upper side wall; the sampling tubes are arranged on side walls of the plexiglass chamber, and the sampling tubes are configured to collect gas in the plexiglass chamber; and the temperature and humidity sensor is arranged in the plexiglass chamber to monitor temperature and humidity information of the gas and soil in the plexiglass chamber; and a gas collection system, including sampling pumps, flow meters, and a plurality of sample collectors and solenoid valves, where one ends of the sampling pumps are connected to the sampling tubes, the flow meters are connected to the other ends of the sampling pumps and one of the solenoid valves respectively, the one of the solenoid valves is also connected to other solenoid valves, and each of the other solenoid valves is connected to one of the sample collectors;

the gas measurement and data processing system includes a gas analyzer, a computer host, a switch and sucking pumps, where one end of each of the sucking pumps is connected to each of the sampling tubes through a solenoid valve, and the other end of each of the sucking pumps is connected to the gas analyzer through the switch; the gas analyzer is connected to the computer host and is configured to measure concentration data of gas in the sampling tubes, and send the concentration data to the computer host for storage.

Preferably, the stainless steel base and the plexiglass chamber are sealed with rubber fasteners.

Preferably, the fans are automatically controlled in a working state through a preset program, and are turned on after the square plexiglass plates are closed, and the fans are configured to mix the gas in the plexiglass chamber.

Preferably, the ON and OFF of the sampling pumps, the flow meters and the solenoid valves are all controlled by preset programs.

Preferably, the sampling tube has a diameter of 6 mm.

A method for field in-situ multi-plot synchronous monitoring of greenhouse gas fluxes, applied to the device for field in-situ multi-plot synchronous monitoring of greenhouse gas fluxes, the method including:

for each independent monitoring channel, acquiring concentration data and sampling time of gas in a plurality of sample collectors;

performing least squares line fitting according to each of the concentration data and sampling time to obtain a relational expression between concentration and sampling time and a correlation coefficient $R^2$, the relational expression between concentration and sampling time being C=b+KT, where C represents the concentration, T represents the time, and k is the coefficient;

when the correlation coefficient is less than a preset threshold, taking any three sets of concentration data and sampling time data and using least squares line fitting, obtaining a relational expression between concentration and sampling time and a correlation coefficient $R^2$, comparing R values, and if the $R^2$ value is the maximum, taking a corresponding value of k; and calculating a greenhouse gas emission flux using the value of k, a calculation formula of the greenhouse gas emission flux being:

$$F = \rho \times k \times h \frac{273}{273+T},$$

where ρ represents the density of greenhouse gas, k represents the change in gas concentration in the automatic open top chamber system per unit time, h represents the height of the automatic open top chamber system, and T represents the average temperature in the automatic open top chamber system during sampling.

According to the specific embodiments provided by the present invention, the present invention discloses the following technical effects:

The present invention provides a device and method for field in-situ multi-plot synchronous monitoring of greenhouse gas fluxes. The device includes at least one independent monitoring channel and a gas measurement and data processing system connected to the independent monitoring channel. The monitoring channel includes: an automatic open top chamber system, including a stainless steel base, a plexiglass chamber, push rods, fans, sampling tubes and a temperature and humidity sensor, where the stainless steel base is arranged in target soil, the bottom of the plexiglass chamber is fixed to the stainless steel base and is transparent, the top of the plexiglass chamber is provided with two movable square plexiglass plates, the square plexiglass plates are connected to the plexiglass chamber through the push rods, and the push rods are configured to close the square plexiglass plates to seal the plexiglass chamber or to open the square plexiglass plates to communicate the plexiglass chamber with the outside world; the fans are arranged on an upper side wall of the plexiglass chamber and at the same position opposite the upper side wall; the sampling tubes are arranged on side walls of the plexiglass chamber, and the sampling tubes are configured to collect gas in the plexiglass chamber; and the temperature and humidity sensor is arranged in the plexiglass chamber to monitor temperature and humidity information of the gas and soil in the plexiglass chamber; and a gas collection system, including sampling pumps, flow meters, and a plurality of sample collectors and solenoid valves, where one ends of the sampling pumps are connected to the sampling tubes, the flow meters are connected to the other ends of the sampling pumps and one of the solenoid valves, the one of the solenoid valves is also connected to other solenoid valves, and each of the other solenoid valves is connected to one of the sample collectors. The gas measurement and data processing system includes a gas analyzer, a computer host, a switch and sucking pumps, where one end of each of the sucking pumps is connected to each of the sampling tubes through a solenoid valve, and the other end of each of the sucking pumps is connected to the gas analyzer through the switch; the gas analyzer is connected to the computer host and is configured to measure concentration data of gas in the sampling tubes, and send the concentration data to the computer host for storage. According to the present invention, the sampling and measurement processes are completed independently, which not only saves manpower and improves sampling efficiency, but also minimizes human errors.

BRIEF DESCRIPTION OF DRAWINGS

In order to illustrate the technical schemes in the embodiments of the present invention or the prior art more clearly, the accompanying drawings to be used in the embodiments will be briefly introduced below. Obviously, the accompanying drawings in the following description are merely some embodiments of the present invention. Those of ordinary skill in the art may obtain other accompanying drawings based on these accompanying drawings without creative efforts.

DESCRIPTION OF REFERENCE NUMERALS

1-Automatic open top chamber system; 2-Gas collection system; 3-Stainless steel base; 4-Push rod; 5-Plexiglass chamber; 6-Fan; 7-Temperature and humidity sensor; 8-Sampling tube; 9-Sampling pump; 10-Flow meter; 11-Sample collector; 12-Solenoid valve; 13-Gas Analyzer; 1-30-First collector; 1-31-Second collector; 1-32-Third collector; 1-34-Fourth collector; 1-1-First solenoid valve; 1-2-Second solenoid valve.

DETAILED DESCRIPTION OF EMBODIMENTS

The technical schemes in the embodiments of the present invention will be clearly and completely described as below with reference to the accompanying drawings in the embodiments of the present invention. Obviously, the described embodiments are only some, not all of, the embodiments of the present invention. All other embodiments obtained by those of ordinary skill in the art based on the embodiments of the present invention without creative effort shall fall into the scope of protection of the present invention.

The object of the present invention is to provide a device for field in-situ multi-plot synchronous monitoring of greenhouse gas fluxes. Accordingly, the sampling and measurement processes are completed independently, which not only saves manpower and improves sampling efficiency, but also minimizes human errors.

In order to make the above objects, features and advantages of the present invention more obvious and easy to understand, the present invention will be further described in detail below in conjunction with the accompanying drawings and specific embodiments.

Figure 1:
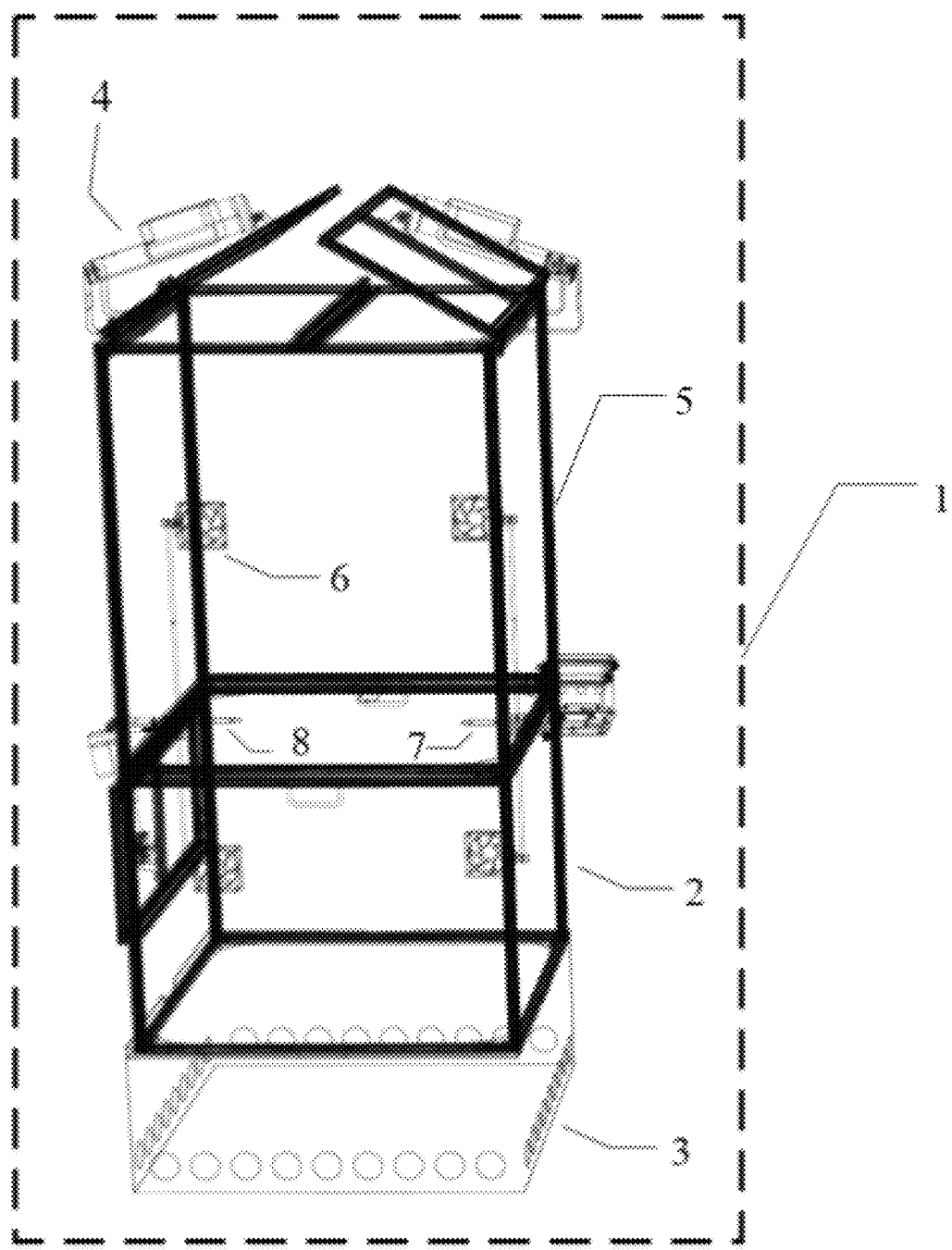
FIG. 1 is a schematic structural diagram of an automatic open top chamber system provided in an embodiment of the present invention.
Figure 2:
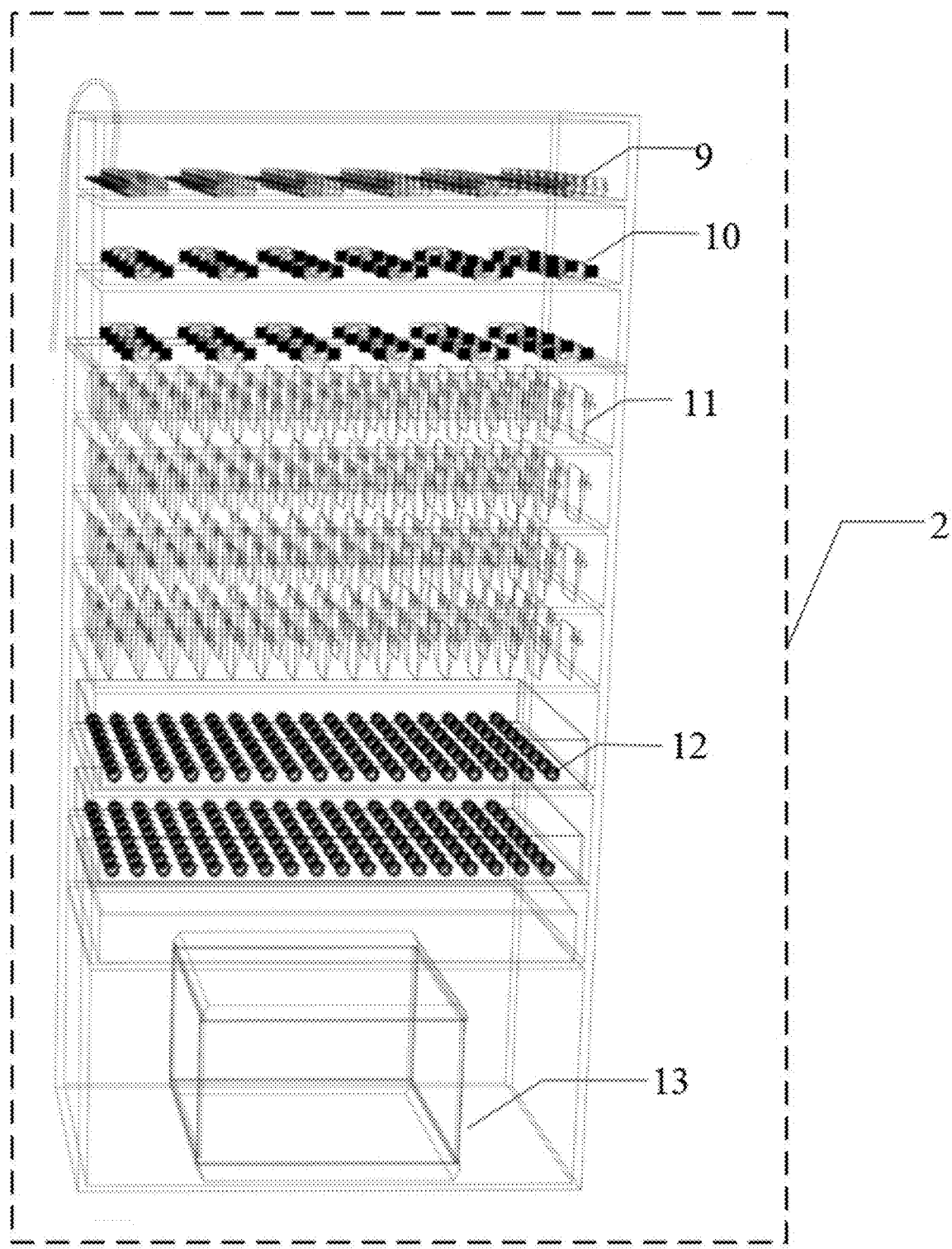
FIG. 2 is a schematic structural diagram of a gas collection system provided in an embodiment of the present invention.
Figure 3:
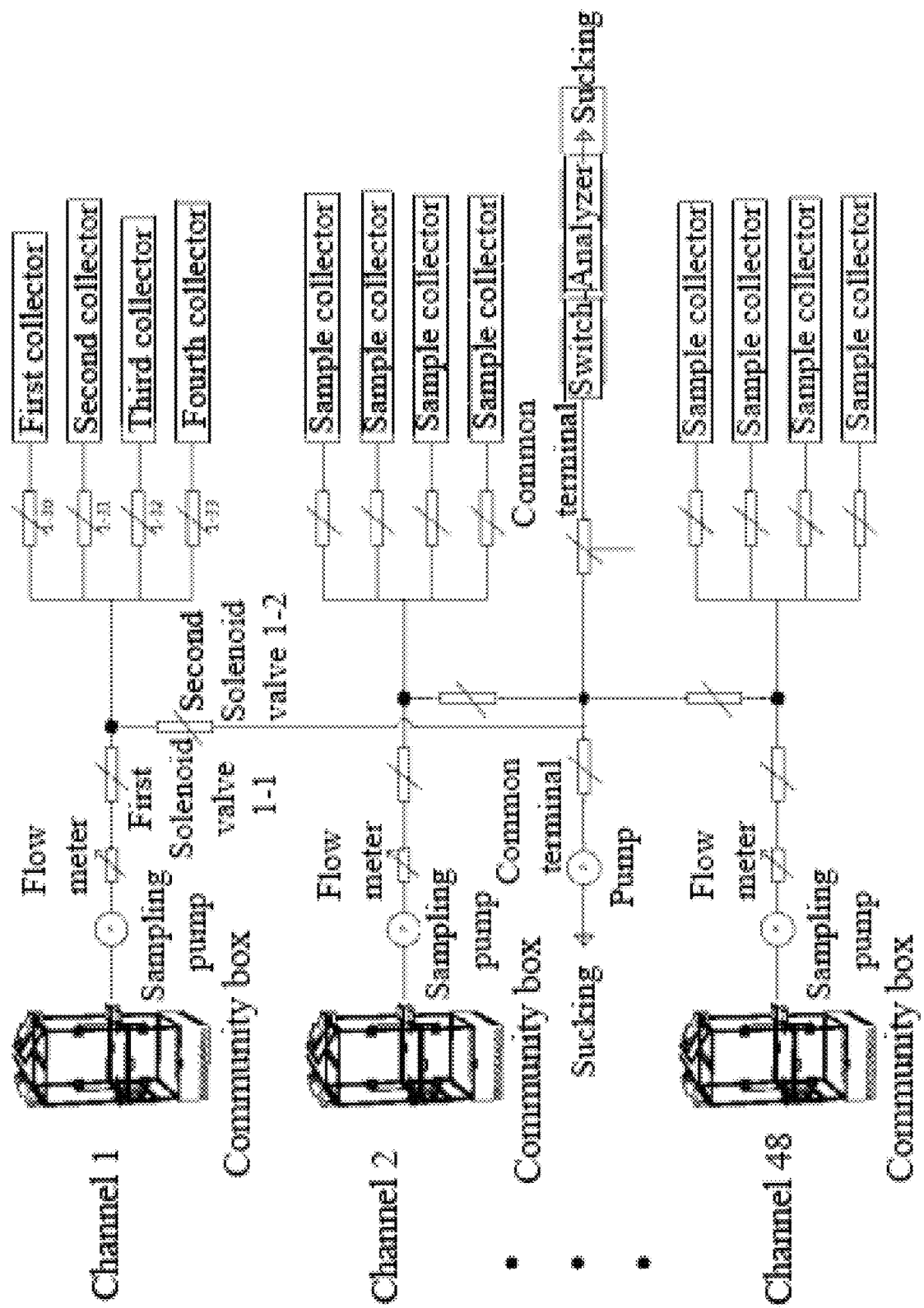
FIG. 3 is a schematic structural diagram of monitoring channels provided in an embodiment of the present invention.

As shown in FIGS. 1 to 3, the automatic open top chamber system 1 of the present invention is composed of a stainless steel base 3, a plexiglass chamber 5, push rods 4 and fans 6, and is configured to create a small closed space in the field during sampling to ensure that gas concentration in the chamber is not affected by natural diffusion. After sampling, the top and sides of the open top chamber are opened, and the internal environment thereof is consistent with the natural environment, not affecting plant growth.

The gas collection system is composed of sampling pumps 9, flow meters 10, sample collectors 11 and solenoid valves 12, and is configured to introduce gas in the automatic open top chamber into the sample collectors according to a set sampling interval and sampling volume for later measurement.

The gas measurement and data processing system is composed of a gas analyzer 13 and a computer host, and is configured to measure, according to set programs, the concentration of greenhouse gas in the sample collectors 11 automatically and calculate an emission flux.

When performing greenhouse gas flux measurement, the stainless steel base 3 is buried in the soil by 15-20 cm 3-5 days in advance and is kept level. After the stainless steel base 3 is stable, the plexiglass chamber 5 is placed into the stainless steel base, and the stainless steel base 3 and the plexiglass chamber 5 are sealed with rubber fasteners. The bottom of the plexiglass chamber 5 is transparent, and the top is provided with square plexiglass plates which are connected to the plexiglass chamber 5 by the push rods 4, and are automatically opened through a control program. The small fans 6 are arranged on an upper side wall of the plexiglass chamber 5 and at the same position opposite the upper side wall. After the top is closed, the fans 6 are controlled through a program to automatically turn on to mix the gas in the chamber. The sampling tubes 8 having a diameter of 6 mm are installed on adjacent side walls, and extend to the outside of the chamber to be connected to Teflon sampling tubes for collecting gas in the chamber. The size of the automatic open top chamber is customized according to crop types and experimental needs. The temperature and humidity sensor 7 is arranged in an automatic sampling chamber to monitor the temperature and humidity of the gas and soil in the chamber.

At a scheduled sampling time, the open top chamber is closed, the first solenoid valve 1-1 is turned on, other solenoid valves remain OFF, the sampling pumps are started, gas is injected into the sample collectors 11 through the flow meters and the first solenoid valve 1-1, and the gas collection volume is recorded through the flow meters. After reaching the rated gas collection volume (which can not only meet the instrument sampling requirements, but also not exceed the maximum capacity of the sample collectors), the first solenoid valve 1-1 is turned off, the sampling pump stops working, the second solenoid valve 1-2 is turned on, and the sucking pumps start working to evacuate the gas in the sampling tubes 8, waiting for the next sampling (with an interval of 10 minutes). When the second sampling time is up, the first solenoid valve 1-1 is turned on, the other solenoid valves remain OFF, the sampling pumps are started, gas is injected into the sample collectors 11 through the flow meters and the first solenoid valve 1-1, and the gas collection volume is recorded through the flow meters. After reaching the rated gas collection volume, the first solenoid valve 1-1 is turned off, the sampling pumps stop working, the second solenoid valve 1-2 is turned on, and the sucking pumps start working to evacuate the gas in the sampling tubes 8, waiting for the next sampling, and so on, until the sampling ends. The collected gas is stored in the sample collectors and the measurement is completed within 24 hours. The ON and OFF of the sampling pumps, the flow meters and the solenoid valves involved in the sampling process are all controlled by programs, and time is set by a user according to his or her needs. Each plot sampling line is an independent unit, and sampling units may be added according to the user's needs. During sampling, the ON of the sampling units may be controlled independently according to the user's needs without interfering with each other.

After the sampling is completed, sample measurement is started. In this case, the first solenoid valve 1-1 is turned off, the gas in the sample collector connected to the first solenoid valve 1-1 is transported to a gas path switching system by the sucking pump and then transported to the gas analyzer for measurement, and the obtained gas concentration data is stored in a gas analyzer host.

According to the above process, the first collector 1-30, the second collector 1-31, the third collector 1-32, and the fourth collector 1-33 are measured sequentially to obtain concentration data C0, C1, C2 and C3, respectively. The concentration data and sampling time (t0, t1, t2, t3) from the gas analyzer host are read by a working computer, and least squares line fitting is used to obtain a relational expression between concentration and sampling time: C=b+kT, where C represents the concentration, and T represents the time. Meanwhile, a correlation coefficient $R^2$ is obtained. When $R^2<0.9$, taking any three sets of concentration and sampling time data and using least squares line fitting, a relational expression between concentration and sampling time and a correlation coefficient $R^2$ are obtained, and R values are compared. If the $R^2$ value is the maximum, a corresponding value of k is taken, and the above process is recorded in the form of a file.

A greenhouse gas emission flux is calculated using the value of k, a formula being as follows:

$$F = \rho \times k \times h \frac{273}{273+T},$$

where ρ represents the density of greenhouse gas, k represents the change in gas concentration in the open top chamber per unit time, h represents the height of the open top chamber, and T represents the average temperature in the open top chamber during sampling.

After the above process ends, the gas collected after channel 2 is measured first, and then measurement is performed on channel 3, channel 4 . . . until all gas samples are measured.

In the specific implementation process, in the present embodiment, the diurnal change of $CH_4$ and $CO_2$ emission fluxes in farmland is monitored in the following mode:

A stainless steel base (with a specification of 80×80×20 cm) is buried in the soil by 20 cm 2 days in advance and is kept level, and then a plexiglass chamber is placed into the stainless steel base and sealed with rubber fasteners, with an automatic open top chamber having a specification of 140× 80×80 cm. It is selected to open channel 1, channel 2 and channel 3, and the sampling interval of four air bags is set to 10 minutes, that is, one flux measurement is completed in 30 minutes, and the next flux measurement is started after 30 minutes, that is, the flux is measured once in 1 hour.

At the scheduled sampling time, the open top chamber is closed to start sampling. Taking plot 1, that is, channel 1, as an example, the first solenoid valve 1-1 is turned on, other solenoid valves remain OFF, and the sampling pumps are started. Gas in the sampling chamberes is injected into the sample collectors 11 through the flow meters and the first solenoid valve 1-1, and the gas sampling volume is recorded through the flow meters. After reaching 500 ml, the first solenoid valve 1-1 is turned off, and the sampling pumps stop working. After waiting for 9 minutes, the second solenoid valve 1-2 is turned on, and the sucking pumps start working to evacuate the gas in the sampling tubes 8. After 1 minute, the second solenoid valve 1-2 is turned off, the sucking pumps stop, the first solenoid valve 1-1 is turned on, the other solenoid valves remain OFF, the sampling pumps are started, and gas is injected into the sample collectors 11 through the flow meters and the first solenoid valve 1-1, and the gas collection volume is recorded through the flow meters. After reaching 500 ml, the first solenoid valve 1-1 is turned off sequentially, the sampling pumps stop working, and the open top chamber is opened, waiting for the next sampling, and so on. Sampling is performed on channel 2 and channel 3 simultaneously, and the sampling process is the same as that in channel 1.

After the sampling is completed, sample measurement is started. In this case, the first solenoid valve 1-1 is turned off, and the gas in the sample collector connected to the first solenoid valve 1-1 is transported to a gas path switching system by the sucking pump and then transported to the gas analyzer for measurement. The first collector 1-30, the second collector 1-31, the third collector 1-32, and the fourth collector 1-33 are measured sequentially to obtain concentration data C0, C1, C2 and C3, respectively. The gas collected after channel 2 is measured, and then measurement is performed on channel 3 sequentially until all gas samples are measured.

The concentration data and sampling time (t0, t1, t2, t3) from the gas analyzer host are read by a working computer, and least squares line fitting is used to obtain a relational expression between concentration and sampling time: C=b+ kT, where C represents the concentration, and T represents the time. Meanwhile, a correlation coefficient $R^2$ is obtained. When $R^2$<0.99, taking any 3 sets of concentration and sampling time data and using least squares line fitting, a relational expression between concentration and sampling time and a correlation coefficient $R^2$ are obtained, and R values are compared. If the $R^2$ value is the maximum, a corresponding value of K is taken.

A greenhouse gas emission flux is calculated using the value of k, a formula being as follows:

$$F=\rho \times k \times h \times 273/(273+T),$$

where ρ represents the density of greenhouse gas, k represents the change in gas concentration in the open top chamber per unit time, h represents the height of the open top chamber, and T represents the average temperature in the open top chamber during sampling.

Figure 4:
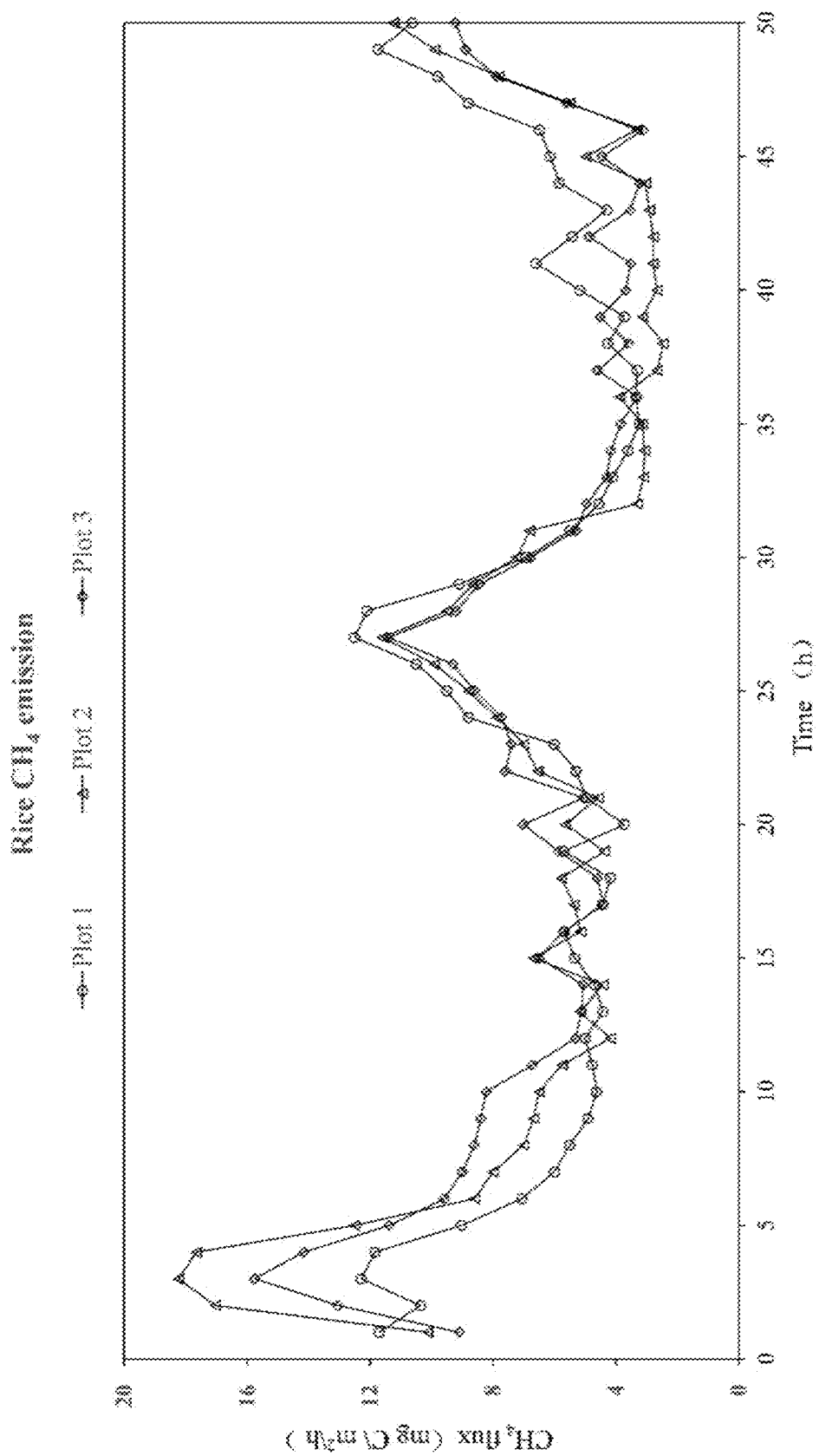
FIG. 4 is a schematic diagram of a diurnal change pattern of rice field methane provided in an embodiment of the present invention.

Sampling is started at 11 o'clock at noon and is continuously performed for 50 hours. As can be seen from FIG. 4, the rice field methane emission flux shows obvious a diurnal change pattern. After the experiment started, it can be seen that the $CH_4$ emission flux is increased rapidly, peaked at around 1:00 at noon, and then gradually decreased. The minimum $CH_4$ emission flux generally appears at 24:00 before dawn, and then keeps at a low value. At around 6 in the morning, the $CH_4$ emission rate begins to increase rapidly, and is peaked at around 1:00 at noon. Judging from the value of the diurnal average emission flux, the emission rate between 9 and 10 in the morning is equivalent to the diurnal average.

Figure 5:
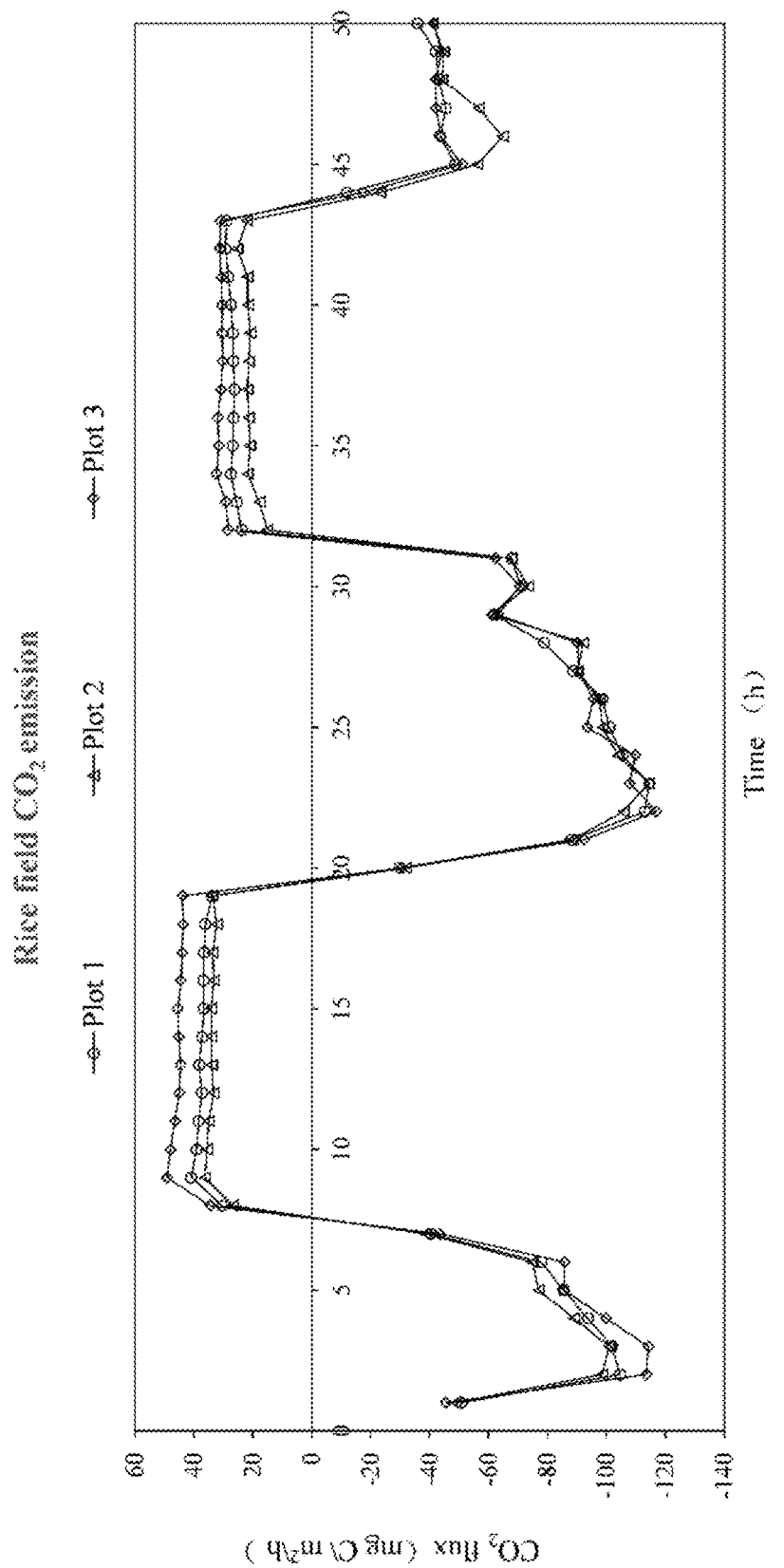
FIG. 5 is a schematic diagram of a diurnal change pattern of carbon dioxide provided in an embodiment of the present invention.

Sampling is started at 11 o'clock at noon and is continuously performed for 50 hours. As can be seen from FIG. 5, the rice field $CO_2$ flux shows an obvious day-night difference. Since a transparent community chamber is adopted in this experiment, photosynthesis of plants could continue during sampling. Therefore, $CO_2$ is absorbed during the day and emitted after the sun sets. The peak $CO_2$ absorption rate during the day appears at 1-2 o'clock at noon, and then the rate gradually decreases. After the sun sets, due to the lack of photosynthesis, $CO_2$ shows a pattern of net emission, with a speed thereof being relatively stable, and until the sun rises, $CO_2$ show a pattern of net absorption.

From the results of 50 consecutive hours, it can be seen that this system has realized simultaneous measurement of rice field greenhouse gas emissions in three plots and obtained diurnal change data of high-frequency emission fluxes.

In addition, in this embodiment, $CH_4$ and $CO_2$ in 48 plots are also monitored synchronously, specifically:

on the basis of Case 1, the rice field methane emission flux is measured at 9:30 in the morning, the data thereof representing the average value of emissions in one day.

There are 48 plots in this experiment, covering 16 different emission reduction measures. The sampling process is the same as Case 1, and the results are shown in Table 1.

The sampling test is performed for a total of 4 days, and this device achieves synchronous measurement of 48 plots. Experimental treatment includes treatment that can significantly reduce $CH_4$ emissions. This device can effectively distinguish between high emission treatment (such as plots 31, 32 and 39) and low emission treatment (such as plots 10, 19 and 20), achieving the purpose of the experiment.

TABLE 1

Synchronous Measurement of 48-Plot $CH_4$ and $CO_2$ Emission Fluxes in Plots 1-21

| | $CH_4$ mg C/m$^2$/h | | | | | $CO_2$ mg C/m$^2$/h | | | | |
|---|---|---|---|---|---|---|---|---|---|---|
| Plot No. | Sep. 15 | Sep. 16 | Sep. 17 | Sep. 18 | | Sep. 14 | Sep. 15 | Sep. 16 | Sep. 17 | Sep. 18 |
| 1 | 0.45 | 0.48 | 0.66 | 0.44 | 0.00 | −38.66 | −23.13 | −38.66 | −29.16 | −1.58 |
| 2 | 0.21 | 0.28 | 0.35 | 0.13 | 0.00 | −48.07 | −28.14 | −48.07 | −47.64 | −6.96 |
| 3 | 0.24 | 0.25 | 0.25 | 0.20 | 0.00 | −58.93 | −36.21 | −58.93 | −54.64 | −11.09 |
| 4 | 0.23 | 0.26 | 0.52 | 0.28 | 0.00 | −55.63 | −34.28 | −55.63 | −53.86 | −10.68 |
| 5 | 0.4 | 0.51 | 0.61 | 0.41 | 0.00 | −54.25 | −31.76 | −54.25 | −52.45 | −8.18 |
| 6 | 0.20 | 0.23 | 0.24 | 0.24 | 0.00 | −33.95 | −20.82 | −33.95 | −30.59 | −2.45 |
| 7 | 0.18 | 0.44 | 0.23 | 0.30 | 0.00 | −48.28 | −29.15 | −48.28 | −48.86 | −7.17 |
| 8 | 0.17 | 0.13 | 0.26 | 0.16 | 0.00 | −22.71 | −14.71 | −22.71 | −22.36 | −1.32 |
| 9 | 0.18 | 0.17 | 0.27 | 0.23 | 0.00 | −43.75 | −36.70 | −43.75 | −53.36 | −1.01 |
| 10 | 0.10 | 0.07 | 0.11 | 0.08 | 0.00 | −40.85 | −26.78 | −40.85 | −45.34 | −5.90 |
| 11 | 0.31 | 0.39 | 0.47 | 0.40 | 0.00 | −57.49 | −34.66 | −57.49 | −59.83 | −2.62 |
| 12 | 0.52 | 0.57 | 0.68 | 0.54 | 0.00 | −52.04 | −30.50 | −52.04 | −49.89 | −7.49 |
| 13 | 0.11 | 0.37 | 0.47 | 0.09 | 0.00 | −53.64 | −31.81 | −53.64 | −51.63 | −8.04 |
| 14 | 0.05 | 0.03 | 0.07 | 0.08 | 0.00 | 10.98 | −25.04 | 10.98 | −40.33 | −3.99 |
| 15 | 0.22 | 0.29 | 0.32 | 0.24 | 0.00 | −58.96 | −36.24 | −58.96 | −51.77 | −3.44 |
| 16 | 0.10 | 0.11 | 0.10 | 0.08 | 0.00 | −50.57 | −30.08 | −50.57 | −50.30 | −7.44 |
| 17 | 0.07 | 0.07 | 0.15 | 0.10 | 0.00 | −24.54 | −14.68 | −24.54 | −21.65 | −2.88 |
| 18 | 0.11 | 0.11 | 0.10 | 0.07 | 0.00 | −48.51 | −32.78 | −48.51 | −49.45 | −6.01 |
| 19 | 0.02 | 0.03 | 0.03 | 0.03 | 0.00 | −52.39 | −31.40 | −52.39 | −49.71 | −6.81 |
| 20 | 0.04 | 0.05 | 0.04 | 0.03 | 0.00 | −53.34 | −32.34 | −53.34 | −50.49 | −7.34 |
| 21 | 0.09 | 0.07 | 0.11 | 0.12 | 0.00 | −57.39 | −35.29 | −57.39 | −47.95 | 3.00 |

TABLE 2

Synchronous Measurement of 48-Plot $CH_4$ and $CO_2$ Emission Fluxes in Plots 22-44

| | $CH_4$ mg C/m$^2$/h | | | | | $CO_2$ mg C/m$^2$/h | | | | |
|---|---|---|---|---|---|---|---|---|---|---|
| Plot No. | Sep. 15 | Sep. 16 | Sep. 17 | Sep. 18 | | Sep. 14 | Sep | Sep. 16 | Sep. 17 | Sep. 18 |
| 22 | 0.05 | 0.03 | 0.07 | 0.07 | 0 | −58.41 | −34.25 | −58.41 | −50.53 | 2.15 |
| 23 | 0.01 | 0.01 | 0 | 0.02 | 0 | −7.4 | −4.63 | −7.4 | −6.53 | −0.58 |
| 24 | 0.11 | 0.35 | 0.12 | 0.31 | 0 | 41.83 | −32.54 | −41.83 | −50.92 | −6.74 |
| 25 | 0.73 | 0.92 | 0.9 | 0.76 | 0 | −52.93 | −31.93 | −52.93 | −50.12 | −5.63 |
| 26 | 2.62 | 0.5 | 0.96 | 0.56 | 0 | −51.5 | −30.59 | −51.5 | −50.38 | −5.97 |
| 27 | 0.79 | 1.31 | 1.43 | 0.67 | 0 | −54.24 | −31.7 | −54.24 | −50.47 | −5.4 |
| 28 | 0.89 | 0.81 | 0.82 | 0.64 | 0 | −49.19 | −31.31 | −49.19 | −46.59 | −6.29 |
| 29 | 1.33 | 1.06 | 0.95 | 0.9 | 0 | −49.87 | −28.84 | −49.87 | −46.89 | −6.23 |
| 30 | 1.24 | 1.33 | 1.56 | 1.2 | 0 | −20.62 | −31.8 | −20.62 | −45.53 | −3.41 |
| 31 | 1.06 | 1.27 | 2.39 | 1.31 | 0 | −49.59 | −28.87 | −49.59 | −47.51 | −5.64 |
| 32 | 1.59 | 1.4 | 1.64 | 1.61 | 0 | −50.38 | −29.79 | −50.38 | −48.24 | −5.68 |
| 33 | 0.48 | 0.63 | 0.49 | 0.47 | 0 | −55.88 | −33.5 | −55.88 | −51.94 | −5.9 |
| 34 | 0.34 | 0.38 | 0.56 | 0.34 | 0 | −51.93 | −30.15 | −51.93 | −48.85 | −5.34 |
| 35 | 0.66 | 0.3 | 0.4 | 0.36 | 0 | −53.74 | −32.19 | −53.74 | −48.88 | −6.27 |
| 36 | 0.32 | 0.37 | 0.35 | 0.29 | 0 | −52.45 | −31.34 | −52.45 | −50.59 | 5.24 |
| 37 | 0.65 | 0.72 | 1.71 | 0.52 | 0 | −48.26 | −29.78 | −48.26 | −46.14 | −6.44 |
| 38 | 0.35 | 0.38 | 0.31 | 0.32 | 0 | −52.85 | −31.66 | −52.85 | −50.44 | −5.69 |
| 39 | 1.03 | 1.6 | 1.49 | 1.28 | 0 | −51.48 | −30.22 | −51.48 | −48.91 | −6.92 |
| 40 | 0.61 | 0.57 | 0.7 | 0.43 | 0 | −54.53 | −33.02 | −54.53 | 50.87 | −6.6 |
| 41 | 0.06 | 0.05 | 0.06 | 0.07 | 0 | −38.32 | −22.76 | −38.32 | −35.84 | −3.53 |
| 42 | 0.83 | 0.6 | 0.79 | 0.97 | 0 | −52.78 | −30.78 | −52.78 | −46.63 | −3.61 |
| 43 | 0.08 | 0.07 | 0.15 | 0.14 | 0 | −50.74 | −30.65 | −50.74 | −48.79 | −5.31 |
| 44 | 0.17 | 0.35 | 0.34 | 0.28 | 0 | −46.88 | −27.7 | −46.88 | −43.69 | −3.62 |

TABLE 3

Synchronous Measurement of 48-Plot $CH_4$ and $CO_2$ Emission Emission

| | $CH_4$ mg C/m$^2$/h | | | | | $CO_2$ mg C/m$^2$/h | | | | |
|---|---|---|---|---|---|---|---|---|---|---|
| Plot No. | Sep. 15 | Sep. 16 | Sep. 17 | Sep. 18 | | Sep. 14 | Sep. 15 | Sep. 16 | Sep. 17 | Sep. 18 |
| 45 | 0.07 | 0.07 | 0.10 | 0.11 | 0.00 | −48.71 | −28.62 | −48.71 | −45.43 | −4.65 |
| 46 | 0.14 | 0.13 | 0.58 | 0.42 | 0.00 | −51.16 | −30.84 | −51.16 | −48.89 | −4.82 |

TABLE 3-continued

Synchronous Measurement of 48-Plot CH₄ and CO₂ Emission Emission

| | $CH_4$ mg C/m²/h | | | | | $CO_2$ mg C/m²/h | | | | |
|---|---|---|---|---|---|---|---|---|---|---|
| Plot No. | Sep. 15 | Sep. 16 | Sep. 17 | Sep. 18 | | Sep. 14 | Sep. 15 | Sep. 16 | Sep. 17 | Sep. 18 |
| 47 | 0.11 | 0.11 | 0.18 | 0.19 | 0.00 | −52.23 | −30.86 | −52.23 | −47.69 | −5.26 |
| 48 | 0.40 | 0.44 | 0.47 | 0.46 | 0.00 | −48.57 | −28.16 | −48.57 | −44.70 | −3.45 |

The present invention has the following beneficial effects:
(1) The On/OFF process of the sampling chamberes is automatically controlled by a program, and synchronous gas extraction, instead of sequential gas extraction and measurement, is performed on all sampling chamberes, effectively avoiding the errors caused by asynchronous sampling time to the experimental results. The sampling and measurement processes are completed independently, which not only saves manpower and improves sampling efficiency, but also minimizes human errors;
(2) The collected gas samples are automatically measured, and the gas samples collected in different time periods of the same plot are measured sequentially during the measurement, which avoids interference from instrument drift on the accuracy of the sample concentration;
(3) Each plot is equipped with an independent gas collection channel, solenoid valve and gas collection pump; after all gas paths are emptied before sampling, gas in an assimilation chamber is used for gas supply and flushing to avoid interference from residual gas in the gas path, and automatic control is achieved;
(4) Sampling and measurement process of each plot is an independent unit; the number of channels can be increased according to the user's needs, and the channel opening time and channel number can be customized according to the user's needs during use to meet personalized needs;
(5) It is compatible with different types of gas analyzers and large community assimilation chamberes, and has strong applicability.

Various embodiments in this specification are described in a progressive manner. Each embodiment focuses on the differences from other embodiments. The same and similar parts among all various embodiments can be referred to each other.

Specific examples are used herein to illustrate the principle and implementations of the present invention. The above description of the embodiments is only used to help understand the method and core idea of the present invention. Meanwhile, for those of ordinary skill in the art, there will be changes in the specific implementations and application scope according to the idea of the present invention. In summary, the content of this specification should not be interpreted as a limitation on the present invention.

What is claimed is:

1. A device for field in-situ multi-plot synchronous monitoring of greenhouse gas fluxes, comprising: a plurality of independent monitoring channels and a gas measurement and data processing system connected to the independent monitoring channels, the monitoring channels comprising:
an automatic open top chamber system, comprising a stainless steel base, a plexiglass chamber, push rods, fans, sampling tubes and a temperature and humidity sensor, wherein the stainless steel base is arranged in target soil, the bottom of the plexiglass chamber is fixed to the stainless steel base and is transparent, the top of the plexiglass chamber is provided with two movable square plexiglass plates, the square plexiglass plates are connected to the plexiglass chamber through the push rods, and the push rods are configured to close the square plexiglass plates to seal the plexiglass chamber or to open the square plexiglass plates to communicate the plexiglass chamber with the outside world; the fans are arranged on an upper side wall of the plexiglass chamber and at the same position opposite the upper side wall; the sampling tubes are arranged on side walls of the plexiglass chamber, and the sampling tubes are configured to collect gas in the plexiglass chamber; and the temperature and humidity sensor is arranged in the plexiglass chamber to monitor temperature and humidity information of the gas and soil in the plexiglass chamber; and
a gas collection system, comprising sampling pumps, flow meters, and a plurality of sample collectors and solenoid valves, wherein one ends of the sampling pumps are connected to the sampling tubes, the flow meters are connected to the other ends of the sampling pumps and one of the solenoid valves respectively, the one of the solenoid valves is also connected to other solenoid valves, and each of the other solenoid valves is connected to one of the sample collectors;
the gas measurement and data processing system comprises a gas analyzer, a computer host, a switch and sucking pumps, wherein one end of each of the sucking pumps is connected to each of the sampling tubes through a solenoid valve, and the other end of each of the sucking pumps is connected to the gas analyzer through the switch; the gas analyzer is connected to the computer host and is configured to measure concentration data of gas in the sampling tubes, and send the concentration data to the computer host for storage;
the fans are automatically controlled in a working state through a preset program, and are turned on after the square plexiglass plates are closed, and the fans are configured to mix the gas in the plexiglass chamber; and ON and OFF of the sampling pumps, the flow meters and the solenoid valves are all controlled by preset programs.

2. The device for field in-situ multi-plot synchronous monitoring of greenhouse gas fluxes according to claim 1, wherein the stainless steel base and the plexiglass chamber are sealed with rubber fasteners.

3. The device for field in-situ multi-plot synchronous monitoring of greenhouse gas fluxes according to claim 1, wherein the sampling tube has a diameter of 6 mm.

4. A method for field in-situ multi-plot synchronous monitoring of greenhouse gas fluxes, applied to the device for field in-situ multi-plot synchronous monitoring of greenhouse gas fluxes according to claim 1, the method comprising:

for each independent monitoring channel, acquiring concentration data and sampling time of gas in a plurality of sample collectors;

performing least squares line fitting according to each of the concentration data and sampling time to obtain a relational expression between concentration and sampling time and a correlation coefficient $R^2$, the relational expression between concentration and sampling time being C=b+kT, where C represents the concentration, T represents the time, and k is the coefficient;

when the correlation coefficient is less than a preset threshold, taking any 3 sets of concentration data and sampling time data and using least squares line fitting, obtaining a relational expression between concentration and sampling time and a correlation coefficient $R^2$, comparing R values, and if the $R^2$ value is the maximum, taking a corresponding value of k; and calculating a greenhouse gas emission flux using the value of k, a calculation formula of the greenhouse gas emission flux being:

$$F = \rho \times k \times h \frac{273}{273+T},$$

where $\rho$ represents the density of greenhouse gas, k represents the change in gas concentration in the automatic open top chamber system per unit time, h represents the height of the automatic open top chamber system, and T represents the average temperature in the automatic open top chamber system during sampling.

\* \* \* \* \*